(12) United States Patent
Mutchler et al.

(10) Patent No.: US 11,160,661 B2
(45) Date of Patent: Nov. 2, 2021

(54) SHOULDER PROSTHESIS GLENOID COMPONENT

(71) Applicant: Tornier SAS, Montbonnot Saint Martin (FR)

(72) Inventors: Austin W. Mutchler, Warsaw, IN (US); Lucile Ferrand, Montbonnot (FR); Yves-Alain Ratron, Grenoble (FR); Jeffrey M. Ondrla, Warsaw, IN (US); Brian C. Hodorek, Winona Lake, IN (US); Pierric Deransart, Saint Martin d'uriage (FR)

(73) Assignee: TORNIER SAS, Montbonnet-Saint Martin (FR)

( * ) Notice: Subject to any disclaimer, the term of this patent is extended or adjusted under 35 U.S.C. 154(b) by 86 days.

(21) Appl. No.: 16/184,670

(22) Filed: Nov. 8, 2018

(65) Prior Publication Data

US 2019/0076261 A1 Mar. 14, 2019

Related U.S. Application Data

(63) Continuation of application No. 13/516,211, filed as application No. PCT/EP2010/069585 on Dec. 14, 2010, now abandoned.

(Continued)

(30) Foreign Application Priority Data

Jan. 21, 2010 (FR) ...................................... 1050376

(51) Int. Cl.
*A61F 2/40* (2006.01)
*A61F 2/30* (2006.01)
(Continued)

(52) U.S. Cl.
CPC ........ *A61F 2/4081* (2013.01); *A61F 2/30749* (2013.01); *A61F 2/4601* (2013.01);
(Continued)

(58) Field of Classification Search
CPC .. A61F 2/34; A61F 2/4657; A61F 2/30; A61F 2/605; A61F 2/4081; A61F 2/4014;
(Continued)

(56) References Cited

U.S. PATENT DOCUMENTS 3,896,504 A 7/1975 Fischer
4,725,280 A 2/1988 Laure
(Continued)

FOREIGN PATENT DOCUMENTS

DE 10123517 C1 11/2002
EP 0581667 2/1994
(Continued)

OTHER PUBLICATIONS

Cementless Fixation Using a Polyethyene Oseo-Integration Peg as Used on the Freeman-Samuelson Knee brochure, produced by Finsbury Instruments Limited London in conjunction with Adrian Tuke Limited, 1982.
(Continued)

*Primary Examiner* — Ann Schillinger
(74) *Attorney, Agent, or Firm* — Duane Morris LLP

(57) ABSTRACT

This shoulder prosthesis glenoid component (2) has on one of its faces an articulation surface ($S_A$) adapted to cooperate with a humeral head and having, on an opposite face ($S_G$) adapted to be immobilized on the glenoid cavity (G) of a shoulder, a keel (4) for anchoring it in the glenoid cavity (G). This keel (4) comprises a body (5) that extends from the opposite face ($S_G$). The keel (4) comprises at least one fin (6) projecting from the body (5) 2 which runs over at least a part of the perimeter of the body (5).

24 Claims, 6 Drawing Sheets

Related U.S. Application Data

(60) Provisional application No. 61/286,286, filed on Dec. 14, 2009.

(51) Int. Cl.
   *A61B 17/80* (2006.01)
   *A61B 17/86* (2006.01)
   *A61F 2/46* (2006.01)
   *A61F 2/28* (2006.01)

(52) U.S. Cl.
   CPC . *A61F 2002/2817* (2013.01); *A61F 2002/305* (2013.01); *A61F 2002/30125* (2013.01); *A61F 2002/30153* (2013.01); *A61F 2002/30171* (2013.01); *A61F 2002/30331* (2013.01); *A61F 2002/30571* (2013.01); *A61F 2002/30878* (2013.01); *A61F 2002/30881* (2013.01); *A61F 2002/30884* (2013.01); *A61F 2002/30901* (2013.01); *A61F 2002/30902* (2013.01); *A61F 2220/0008* (2013.01); *A61F 2220/0025* (2013.01); *A61F 2220/0033* (2013.01); *A61F 2230/005* (2013.01); *A61F 2230/0008* (2013.01); *A61F 2230/0019* (2013.01)

(58) Field of Classification Search
   CPC .. A61F 2/4612; A61F 2/40; A61F 2/32; A61F 2002/4018; A61F 2002/4022; A61F 2/4059; A61F 2002/30736; A61F 2002/30891; A61F 2002/30578; A61F 2002/30649; A61F 2002/30884; A61F 2/4601; A61F 2002/2817; A61F 2002/30125; A61F 2002/30153; A61F 2002/30171; A61F 2002/30331; A61F 2002/305; A61F 2002/30571; A61F 2002/30878; A61F 2002/30881; A61F 2002/30901; A61F 2002/30902; A61F 220/0008; A61F 2220/0025; A61F 2220/0033; A61F 2230/0008; A61F 2230/0019; A61F 2230/005; A61B 5/4571; A61A 612/30749
   See application file for complete search history.

(56) References Cited

U.S. PATENT DOCUMENTS

| | | | |
|---|---|---|---|
| 4,986,833 A | 1/1991 | Worland | |
| 5,032,132 A | 7/1991 | Matsen, III et al. | |
| 5,033,036 A | 7/1991 | Ohmori et al. | |
| 5,080,673 A * | 1/1992 | Burkhead | A61F 2/40 623/19.11 |
| 5,108,446 A | 4/1992 | Wagner | |
| 5,458,637 A | 10/1995 | Hayes | |
| 5,489,309 A | 2/1996 | Lackey et al. | |
| 5,489,311 A | 2/1996 | Cipolletti | |
| 5,531,973 A | 7/1996 | Sarv | |
| 5,662,657 A | 9/1997 | Carn | |
| 5,702,447 A * | 12/1997 | Walch | A61B 17/809 606/309 |
| 5,776,202 A | 7/1998 | Copf et al. | |
| 5,800,551 A | 9/1998 | Williamson et al. | |
| 5,954,722 A | 9/1999 | Bono | |
| 6,102,954 A | 8/2000 | Albrektsson et al. | |
| 6,171,342 B1 | 1/2001 | O'Neil et al. | |
| 6,228,119 B1 | 5/2001 | Ondrla et al. | |
| 6,228,120 B1 | 5/2001 | Leonard et al. | |
| 6,406,495 B1 * | 6/2002 | Schoch | A61F 2/4081 623/19.11 |
| 6,508,841 B2 | 1/2003 | Martin et al. | |
| 6,514,287 B2 | 2/2003 | Ondrla et al. | |
| 6,673,115 B2 | 1/2004 | Resch et al. | |
| 6,679,916 B1 | 1/2004 | Frankle et al. | |
| 6,699,289 B2 | 3/2004 | Iannotti et al. | |
| 6,761,740 B2 | 7/2004 | Tornier | |
| 6,783,549 B1 | 8/2004 | Stone et al. | |
| 6,790,234 B1 | 9/2004 | Frankle | |
| 6,860,903 B2 | 3/2005 | Mears et al. | |
| 6,911,047 B2 | 6/2005 | Rockwood et al. | |
| 6,953,478 B2 | 10/2005 | Bouttens et al. | |
| 6,969,406 B2 | 11/2005 | Tornier | |
| 7,160,328 B2 | 1/2007 | Rockwood et al. | |
| 7,169,184 B2 | 1/2007 | Pria | |
| 7,175,663 B1 | 2/2007 | Stone | |
| 7,175,665 B2 | 2/2007 | German et al. | |
| 7,204,854 B2 | 4/2007 | Guederian et al. | |
| 7,316,715 B2 | 1/2008 | Plaskon | |
| 7,462,197 B2 | 12/2008 | Tornier | |
| 7,462,199 B2 | 12/2008 | Justin et al. | |
| 7,604,665 B2 | 10/2009 | Iannotti et al. | |
| 7,608,109 B2 | 10/2009 | Dalla Pria | |
| 7,611,539 B2 | 11/2009 | Bouttens et al. | |
| 7,621,961 B2 | 11/2009 | Stone | |
| 7,637,928 B2 | 12/2009 | Fernandez | |
| 7,648,530 B2 | 1/2010 | Habermeyer et al. | |
| 7,666,522 B2 | 2/2010 | Justin et al. | |
| 7,753,959 B2 | 7/2010 | Berelsman et al. | |
| 7,766,969 B2 | 8/2010 | Justin et al. | |
| 7,854,768 B2 | 12/2010 | Wiley et al. | |
| 7,892,287 B2 | 2/2011 | Deffenbaugh | |
| 7,922,769 B2 | 4/2011 | Deffenbaugh et al. | |
| 7,927,335 B2 | 4/2011 | Deffenbaugh et al. | |
| 7,993,408 B2 | 8/2011 | Meridew et al. | |
| 8,007,523 B2 | 8/2011 | Wagner et al. | |
| 8,048,161 B2 | 11/2011 | Guederian et al. | |
| 8,062,376 B2 | 11/2011 | Shultz et al. | |
| 8,070,820 B2 | 12/2011 | Winslow et al. | |
| 8,092,545 B2 | 1/2012 | Coon et al. | |
| 8,206,453 B2 | 6/2012 | Cooney, III et al. | |
| 8,231,683 B2 | 7/2012 | Lappin et al. | |
| 8,241,365 B2 | 8/2012 | Williams, Jr. et al. | |
| 8,287,600 B2 | 10/2012 | Angibaud | |
| 8,308,807 B2 | 11/2012 | Seebeck et al. | |
| 8,357,201 B2 | 1/2013 | Mayer et al. | |
| 8,361,157 B2 | 1/2013 | Bouttens et al. | |
| 8,425,614 B2 | 4/2013 | Winslow et al. | |
| 8,444,680 B2 | 5/2013 | Dooney, Jr. et al. | |
| 8,449,617 B1 | 5/2013 | McDaniel et al. | |
| 8,454,702 B2 | 6/2013 | Smits et al. | |
| 8,465,548 B2 | 6/2013 | Long | |
| 8,480,750 B2 | 7/2013 | Long | |
| 8,532,806 B1 | 9/2013 | Masson | |
| 8,556,902 B2 | 10/2013 | Ek et al. | |
| 8,556,980 B2 | 10/2013 | Deffenbaugh | |
| 8,556,981 B2 | 10/2013 | Jones et al. | |
| 8,591,591 B2 | 11/2013 | Winslow et al. | |
| 8,597,334 B2 | 12/2013 | Mocanu | |
| 8,632,597 B2 | 1/2014 | Lappin | |
| 8,690,951 B2 | 4/2014 | Baum et al. | |
| 8,753,402 B2 | 6/2014 | Winslow et al. | |
| 8,790,402 B2 | 7/2014 | Monaghan et al. | |
| 8,840,676 B2 | 9/2014 | Belew | |
| 8,864,834 B2 | 10/2014 | Boileau et al. | |
| 8,961,611 B2 | 2/2015 | Long | |
| 9,114,017 B2 | 8/2015 | Lappin | |
| 9,233,003 B2 | 6/2016 | Roche et al. | |
| 9,498,345 B2 | 11/2016 | Burkhead et al. | |
| 9,545,311 B2 | 1/2017 | Courtney, Jr. et al. | |
| 9,629,725 B2 | 4/2017 | Gargac et al. | |
| 10,034,757 B2 | 7/2018 | Kovacs et al. | |
| 10,064,734 B2 | 9/2018 | Burkhead et al. | |
| 10,251,755 B2 | 4/2019 | Boileau et al. | |
| 10,342,669 B2 | 7/2019 | Hopkins | |
| 10,357,373 B2 | 7/2019 | Gargac et al. | |
| 10,524,922 B2 | 1/2020 | Courtney, Jr. et al. | |
| 10,722,374 B2 | 7/2020 | Hodorek et al. | |
| 2001/0037153 A1 * | 11/2001 | Rockwood, Jr. | A61F 2/4081 623/19.13 |
| 2002/0095214 A1 | 7/2002 | Hyde, Jr. | |
| 2003/0055507 A1 | 3/2003 | McDevitt et al. | |
| 2003/0149485 A1 | 8/2003 | Tornier | |
| 2004/0030394 A1 | 2/2004 | Horber | |

(56) References Cited

U.S. PATENT DOCUMENTS

| | | | |
|---|---|---|---|
| 2004/0059424 A1* | 3/2004 | Guederian | A61B 17/864 623/19.11 |
| 2004/0106928 A1 | 6/2004 | Ek | |
| 2004/0220673 A1 | 11/2004 | Pria | |
| 2004/0220674 A1 | 11/2004 | Pria | |
| 2005/0049709 A1* | 3/2005 | Tornier | A61F 2/40 623/19.13 |
| 2005/0060039 A1 | 3/2005 | Cyprien | |
| 2005/0143831 A1 | 6/2005 | Justin et al. | |
| 2005/0149044 A1 | 7/2005 | Justin et al. | |
| 2005/0261775 A1 | 11/2005 | Baum et al. | |
| 2005/0278030 A1 | 12/2005 | Tornier | |
| 2006/0074353 A1 | 4/2006 | Deffenbaugh et al. | |
| 2006/0100714 A1 | 5/2006 | Ensign | |
| 2006/0122705 A1 | 6/2006 | Morgan | |
| 2006/0142865 A1 | 6/2006 | Hyde, Jr. | |
| 2006/0200248 A1 | 9/2006 | Beguin et al. | |
| 2006/0200249 A1 | 9/2006 | Beguin et al. | |
| 2007/0016304 A1 | 1/2007 | Chudik | |
| 2007/0055380 A1 | 3/2007 | Berelsman et al. | |
| 2007/0100458 A1 | 5/2007 | Dalla Pria | |
| 2007/0142921 A1 | 6/2007 | Lewis et al. | |
| 2007/0156246 A1 | 7/2007 | Meswania et al. | |
| 2007/0179624 A1 | 8/2007 | Stone et al. | |
| 2007/0219638 A1 | 9/2007 | Jones et al. | |
| 2007/0244563 A1 | 10/2007 | Roche et al. | |
| 2007/0244564 A1* | 10/2007 | Ferrand | A61F 2/4081 623/19.13 |
| 2008/0183297 A1 | 7/2008 | Boileau et al. | |
| 2008/0269906 A1 | 10/2008 | Iannotti et al. | |
| 2008/0294268 A1 | 11/2008 | Baum et al. | |
| 2008/0306601 A1 | 12/2008 | Dreyfuss | |
| 2009/0125113 A1 | 5/2009 | Guederian et al. | |
| 2009/0149961 A1 | 6/2009 | Dallmann | |
| 2009/0204225 A1 | 8/2009 | Meridew et al. | |
| 2009/0216332 A1 | 8/2009 | Splieth et al. | |
| 2009/0281630 A1 | 11/2009 | Delince et al. | |
| 2009/0292364 A1 | 11/2009 | Linares | |
| 2010/0016975 A1 | 1/2010 | Iannotti et al. | |
| 2010/0023068 A1 | 1/2010 | Bouttens et al. | |
| 2010/0049327 A1 | 2/2010 | Isch et al. | |
| 2010/0087927 A1 | 4/2010 | Roche et al. | |
| 2010/0161066 A1 | 6/2010 | Iannotti et al. | |
| 2010/0217399 A1 | 8/2010 | Groh | |
| 2010/0228352 A1 | 9/2010 | Courtney et al. | |
| 2010/0234959 A1 | 9/2010 | Roche et al. | |
| 2010/0274359 A1 | 10/2010 | Brunnarius et al. | |
| 2010/0291401 A1 | 11/2010 | Medina et al. | |
| 2010/0331990 A1 | 12/2010 | Mroczkowski | |
| 2011/0035013 A1 | 2/2011 | Winslow et al. | |
| 2011/0118846 A1 | 5/2011 | Katrana et al. | |
| 2011/0144760 A1 | 6/2011 | Wong et al. | |
| 2011/0190899 A1 | 8/2011 | Pierce et al. | |
| 2011/0282393 A1 | 11/2011 | Garlach et al. | |
| 2012/0004733 A1 | 1/2012 | Hodorek et al. | |
| 2012/0029647 A1 | 2/2012 | Winslow et al. | |
| 2012/0130498 A1 | 5/2012 | Long | |
| 2012/0165954 A1 | 6/2012 | Nimal | |
| 2012/0191201 A1 | 7/2012 | Smits et al. | |
| 2012/0209392 A1 | 8/2012 | Angibaud et al. | |
| 2012/0221112 A1 | 8/2012 | Lappin | |
| 2012/0232670 A1 | 9/2012 | Bojarski et al. | |
| 2012/0239156 A1 | 9/2012 | De Wilde et al. | |
| 2012/0253467 A1 | 10/2012 | Frankle | |
| 2012/0277880 A1 | 11/2012 | Winslow et al. | |
| 2013/0018483 A1 | 1/2013 | Li et al. | |
| 2013/0053968 A1 | 2/2013 | Nardini et al. | |
| 2013/0096631 A1 | 4/2013 | Leung et al. | |
| 2013/0110470 A1 | 5/2013 | Vanasse et al. | |
| 2013/0144393 A1 | 6/2013 | Mutchler | |
| 2013/0150972 A1 | 6/2013 | Iannotti et al. | |
| 2013/0150973 A1 | 6/2013 | Splieth et al. | |
| 2013/0150975 A1 | 6/2013 | Iannotti et al. | |
| 2013/0226309 A1 | 8/2013 | Daigo et al. | |
| 2013/0231754 A1 | 9/2013 | Daigo et al. | |
| 2013/0253656 A1 | 9/2013 | Long | |
| 2013/0261751 A1 | 10/2013 | Lappin | |
| 2013/0261752 A1 | 10/2013 | Lappin et al. | |
| 2013/0264749 A1 | 10/2013 | Jones et al. | |
| 2013/0282135 A1 | 10/2013 | Sun et al. | |
| 2014/0025173 A1 | 1/2014 | Cardon et al. | |
| 2014/0142711 A1 | 5/2014 | Maroney et al. | |
| 2014/0194995 A1 | 7/2014 | Koka | |
| 2014/0257499 A1 | 9/2014 | Winslow et al. | |
| 2014/0277180 A1 | 9/2014 | Paolino et al. | |
| 2014/0371863 A1 | 12/2014 | Vanasse et al. | |
| 2015/0073424 A1 | 3/2015 | Couture et al. | |
| 2015/0094819 A1 | 4/2015 | Iannotti et al. | |
| 2015/0142122 A1 | 5/2015 | Bickley et al. | |
| 2015/0150688 A1 | 6/2015 | Vanasse et al. | |
| 2015/0272741 A1 | 10/2015 | Taylor et al. | |
| 2015/0305877 A1 | 10/2015 | Gargac et al. | |
| 2016/0045323 A1 | 2/2016 | Kovacs et al. | |
| 2016/0166392 A1 | 6/2016 | Vanasse et al. | |
| 2016/0270922 A1 | 9/2016 | Pressacco et al. | |
| 2016/0287401 A1 | 10/2016 | Muir et al. | |
| 2016/0310285 A1 | 10/2016 | Kovacs et al. | |
| 2016/0324649 A1 | 11/2016 | Hodorek et al. | |
| 2017/0027709 A1 | 2/2017 | Winslow et al. | |
| 2017/0042687 A1 | 2/2017 | Boileau et al. | |
| 2017/0042690 A1 | 2/2017 | Burkhead et al. | |
| 2017/0172764 A1 | 6/2017 | Muir et al. | |
| 2017/0273795 A1 | 9/2017 | Neichel et al. | |
| 2017/0273801 A1 | 9/2017 | Hodorek et al. | |
| 2018/0064537 A1 | 3/2018 | Pressacco et al. | |
| 2018/0078377 A1 | 3/2018 | Gargac et al. | |
| 2018/0161169 A1 | 6/2018 | Cardon et al. | |
| 2018/0243102 A1 | 8/2018 | Burkhead, Jr. et al. | |
| 2020/0030108 A1 | 1/2020 | Orphanos et al. | |
| 2020/0179126 A1 | 6/2020 | Courtney, Jr. et al. | |
| 2020/0237519 A1 | 7/2020 | Ball et al. | |

FOREIGN PATENT DOCUMENTS

| | | | |
|---|---|---|---|
| EP | 0776636 B1 | 9/2000 | |
| EP | 1323395 A2 | 7/2003 | |
| EP | 1013246 B1 | 10/2003 | |
| EP | 1064890 B1 | 9/2005 | |
| EP | 1488764 B1 | 12/2006 | |
| EP | 1762201 A1 * | 3/2007 | A61F 2/4081 |
| EP | 1762201 A1 | 3/2007 | |
| EP | 1515758 B1 | 3/2009 | |
| EP | 2057970 A2 | 5/2009 | |
| EP | 1639966 B1 | 9/2009 | |
| EP | 1927328 B1 | 1/2011 | |
| EP | 1902689 B1 | 11/2011 | |
| EP | 1996125 B1 | 5/2013 | |
| EP | 2335655 B1 | 7/2013 | |
| EP | 1951161 B1 | 4/2014 | |
| EP | 1973498 B1 | 4/2014 | |
| EP | 2481376 B1 | 4/2014 | |
| EP | 2601912 B1 | 7/2016 | |
| FR | 2567019 | 1/1986 | |
| FR | 2739151 A1 | 3/1997 | |
| FR | 2776506 B1 | 8/2000 | |
| FR | 2955247 A1 | 7/2011 | |
| FR | 2971144 A1 | 8/2012 | |
| FR | 2977791 B1 | 7/2014 | |
| WO | WO 2011/073169 | 6/2011 | |
| WO | WO 2011/150180 A2 | 12/2011 | |
| WO | WO 2015/068035 | 5/2015 | |
| WO | WO 2015/103090 | 7/2015 | |
| WO | WO 2017/007565 | 1/2017 | |
| WO | WO 2019/079104 | 4/2019 | |

OTHER PUBLICATIONS

European Search Report issued in European Patent Application No. 10155440, dated Aug. 9, 2010, 6 pages.

File History for U.S. Appl. No. 12/398,750, filed Mar. 5, 2009.

International Search Report and Written Opinion issued in PCT/EP2010/069585, dated Apr. 11, 2011, 9 pages.

(56) References Cited

OTHER PUBLICATIONS

Anatomical Shoulder™ Inverse/Reverse System Surgical Technique, Product Brochure, Zimmer, Inc., published 2006, in 32 pages.
Arthrex, "Arthrex Releases Univers Revers™ Shoulder Arthroplasty System in the United States—First Surgery Successfully Performed in Chillicothe, OH", Jun. 18, 2013.
Biomet, "Comprehensive® Reverse Shoulder System", 2013.
Boileau et al., "Cemented polyethylene versus uncemented metal-backed glenoid components in total shoulder arthroplasty: A prospective, double-blind, randomized study," Journal of Shoulder and Elbow Surgery, Jul./Aug. 2002, vol. 11, Issue 4, pp. 351-359.
Boileau et al., "Metal-backed glenoid implant with polyethylene insert is not a viable long-term therapeutic option," Journal of Shoulder and Elbow Surgery, Feb. 2015, pp. 1-10.
Castagna et al., "Mid-term results of a metal-backed glenoid component in total shoulder replacement," The Journal of Bone and Joint Surgery, Oct. 2010, vol. 92-B, No. 10, pp. 1410-1415.
Clement et al., "An uncemented metal-backed glenoid component in total shoulder arthroplasty for osteoarthritis: factors affecting survival and outcome," The Japanese Orthopaedic Association, published online Sep. 26, 2012, vol. 18, pp. 22-28.
DJO Surgical, Reverse® shoulder prosthesis Surgical Technique, Feb. 2008.
Eclipse™ Stemless Shoulder Prosthesis, Surgical Technique Guide, Anthrex GmbH, 2014, in 12 pages.
Epoca Shoulder Arthroplasty System, Synthes, Inc., Apr. 2008, in 4 pages.
Epoca Shoulder Arthroplasty System—Stem and Glenoid Technique Guide, Synthes, Inc., Apr. 2008, in 56 pages.
Innovative Design Orthopaedics, "Verso® Shoulder Surgical Technique", 2013.
Kany et al., "A convertible shoulder system: is it useful in total shoulder arthroplasty revisions?" International Orthopaedics, published online Oct. 16, 2014, vol. 39, pp. 299-304.
Katz et al., "New design of a cementless glenoid component in unconstrained shoulder arthroplasty: a prospective medium-term analysis of 143 cases," published online Oct. 27, 2012, vol. 23, pp. 27-34.
Montoya et al., "Midterm results of a total shoulder prosthesis fixed with a cementless glenoid component," Journal of Shoulder and Elbow Surgery, May 2013, vol. 22, Issue 5, pp. 628-635.
SMR Axioma® TT Metal Back Surgical Technique, Product Brochure, Lima Corporate, dated Sep. 2013, in 48 pages.
Taunton et al., "Total Shoulder Arthroplasty with a Metal-Backed, Bone-Ingrowth Glenoid Component," The Journal of Bone and Joint Surgery, Oct. 2008, vol. 90-A, Issue 10, pp. 2180-2188.
Teissier et al., "The TESS reverse shoulder arthroplasty without a stem in the treatment of cuff-deficient shoulder conditions: clinical and radiographic results," Journal of Shoulder and Elbow Surgery, Jan. 2015, vol. 24, Issue 1, pp. 45-51.
The Anatomical Shoulder™: A true system approach, Product Brochure, Zimmer UK Ltd, printed 2006, in 6 pages.
Univers Revers™ Total Shoulder System, Surgical Technique Guide, Anthrex Inc., Version D, revised Jul. 2, 2015, in 28 pages.

\* cited by examiner

SHOULDER PROSTHESIS GLENOID COMPONENT

CROSS REFERENCE TO RELATED APPLICATIONS

The present application is a continuation of U.S. application Ser. No. 13/516,211, filed Jan. 25, 2013, which is a national phase of PCT Application No. PCT/EP2010/069585, filed Dec. 14, 2010, which claims the priority benefit of U.S. Provisional Application No. 61/286,286, filed Dec. 14, 2009, which are hereby incorporated in their by reference in its entirety.

The present invention concerns a shoulder prosthesis glenoid component.

In the field of shoulder prostheses, it is routine to use a glenoid component comprising an articulation surface, a bearing surface on a shoulder glenoid cavity and means for fixing the component in the glenoid cavity. These means may constitute screws, pegs, rods or keels or combinations of these means. It is known in particular from US-A-2001/0037153 to produce components provided with cylindrical studs of circular section.

These solutions have drawbacks linked to the mode of implanting the glenoid component in the glenoid cavity of the shoulder. The conjugate effects of movement of the arm and aging of the component tend to loosen the fixing of the component and cause deterioration of its fixing means. In particular, the eccentric forces exerted by the head of the humerus on the articulation surface are liable to reduce the firmness of a keel-type fixing of the glenoid component, in that part of the keel is anchored in the spongy part of the bone. Moreover, studs such as are known from the aforementioned document are not able to block rotation of the components in the glenoid cavity.

It is these drawbacks that the invention aims more particularly to remedy by proposing a new keel-type glenoid component the fixing of which is made reliable and durable.

To this end, the invention provides a shoulder prosthesis glenoid component having on one of its faces an articulation surface adapted to cooperate with a humeral head and an opposite face. This component further includes a keel for anchoring it in the glenoid cavity of a shoulder, comprising a body that extends from an opposite face adapted to be immobilized in the glenoid cavity. This component is characterized in that the keel comprises at least one fin projecting from the body which runs over at least a part of the perimeter of the body.

Thanks to the invention, the fixing of the component in the glenoid cavity is improved compared to fixing using a keel with no fins, the free spaces created by the fins encouraging locking of the component in the glenoid cavity by bone growth in these spaces. Adding fins to the keel of the glenoid component therefore makes it possible to improve the stability and the service life of the prosthesis.

According to advantageous but non-mandatory aspects of the invention, such a component may incorporate one or more of the following features, in all technically permissible combinations:

The body of the keel has in cross section a non-circular peripheral contour.
The fin or at least one of the fins has a helicoidal shape and winds around the body.
The body comprises at least one internal passage opening onto the external surface of the body and connected to an orifice for injecting a fluid such as a bone substitute or a solution containing growth factors.
The fin or at least one of the fins extends in a plane substantially perpendicular to a longitudinal main axis of the body.
The body comprises at least two separate cylindrical parts the respective axes of which are substantially parallel to each other and between which the fin or fins extend(s).
The body includes at least one external peripheral groove for receiving an elastic ring adapted to expand in the glenoid cavity.
The body has a star-shaped cross section including at least three branches and the keel has an eccentric position relative to a central axis of the component.
The fin or at least one of the fins has a substantially semicircular peripheral contour.
The keel comprises a first series of substantially parallel fins.
The keel further comprises at least one second series of parallel fins, of width greater than that of the first fins and placed at a distance from the opposite face along a longitudinal main axis of the body less than that of the first series of fins.
The fins of the or each second series of fins have a shape that is geometrically similar to the shape of the opposite face.
The articulation surface is carried by an element adapted to be mounted in a preferably metal shell of the component carrying the opposite face and in one piece with the body of the keel.
The body of the keel comprises a flexible sheath provided with the fin or fins into which a part in one piece with the opposite face is adapted to fit.
The fins are made of a deformable material chosen from materials such as polyethylene or other polymer materials.
The body of the keel includes a hole passing through the body.

The invention will be better understood and other advantages thereof will become more clearly apparent in the light of the following description of a glenoid component of various embodiments of the invention given by way of example only and with reference to the drawings, in which.

The glenoid component 2 represented in FIGS. 1 to 15 is adapted to be fixed on the glenoid cavity G of a shoulder of a human being. The glenoid component 2 has an articulation surface $S_A$, here generally concave, intended to cooperate with a humeral component, not shown, that may be prosthetic or natural. The surface $S_A$ may equally be convex in order to cooperate with a concave spherical surface of the humeral component, notably in the case of a reversed prosthesis.

The component 2 has on the side opposite its articulation surface $S_A$ a face $S_G$ that bears on the glenoid cavity G. This face $S_G$ can be superposed on that of the glenoid cavity and is generally of convex shape. However, as a function of the shape of the socket G, the face $S_G$ may have other shapes, notably plane in order to fit a flat-bottomed glenoid cavity G.

For fixing it into the glenoid cavity G, the glenoid component 2 includes an anchor keel 4. This keel 4 consists mainly of a body 5 extending from the central region of the bearing face $S_G$. This keel is intended to be immobilized in a drilled hole P or the like of corresponding size and shape produced in the socket G. In practice, the keel 4 may have an external envelope of varied dimensions and shapes so as to have in cross section a non-circular peripheral contour in order to block rotation of the component in the glenoid cavity G. In particular, the keel 4 may preferably have an envelope of truncated pyramid shape, the base of which may be substantially square or rectangular. Alternatively, this envelope may be of frustoconical shape with a substantially elliptical base. In all cases, the geometry of the body 5 defines a longitudinal main axis X-X' transverse to the articulation surface $S_A$ and to the bearing face $S_G$.

Figure 1:
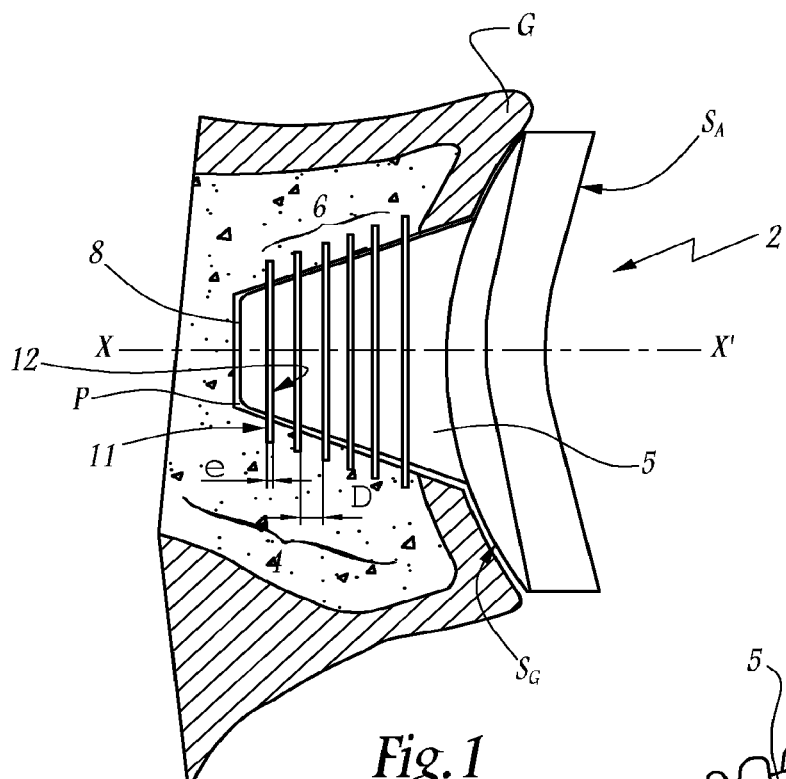
FIG. 1 is a front view of a glenoid component of the invention, corresponding to a generic embodiment and shown implanted in the glenoid cavity of a shoulder.

As shown generically in FIG. 1, the keel 4 of the component 2 is provided with at least one fin 6. Each fin is constituted of a wall projecting from the body 5 and has two substantially parallel opposite surfaces 11 and 12 separated by a distance e that defines the thickness of the fin. The fin or fins may run along part or the whole of the perimeter of the keel 4, this perimeter being defined by the peripheral surface enveloping the body 5 around the longitudinal axis X-X' from the face $S_G$ at the axially opposite end 8 of this body. For fixing the implant, the distance between the bearing surface $S_G$ and the first fin 6 advantageously corresponds to the average thickness of cortical bone tissue constituting the surface of the glenoid cavity. Thus during insertion of the prosthesis all of the fins 6 are inserted into the spongy bone tissue of the glenoid cavity, trapping the cortical structure between the fins 6 and the bearing surface $S_G$ in order to render extraction of the prosthesis more difficult.

References common to the specific embodiments described hereinafter remain unchanged. The references that differentiate these embodiments include a numerical prefix corresponding to the numbering of the embodiment described.

Figure 2:
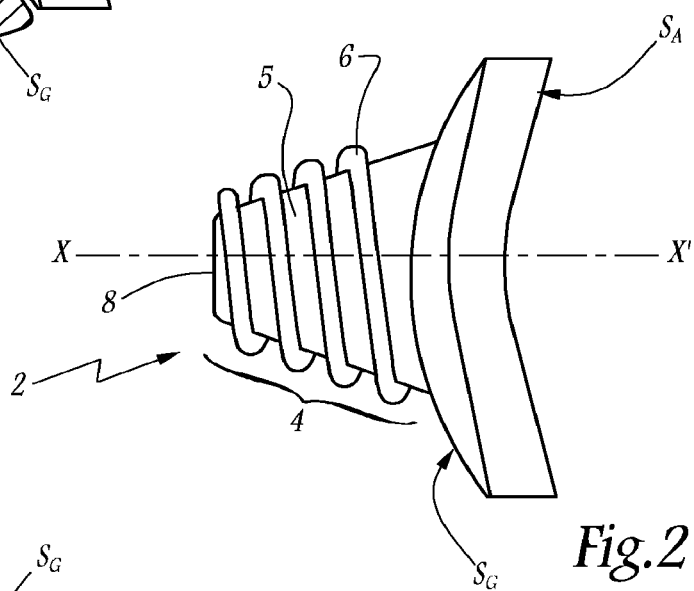
FIG. 2 is a front view of a glenoid component according to a specific first embodiment of the invention.

In the first embodiment represented in FIG. 2 the keel 4 is provided with a single fin 6. This fin 6 is of helicoidal shape and winds around the body 5 of the keel 4 along the longitudinal main axis X-X' and with a pitch that either is constant or varies. The helicoid described by the fin 6 advantageously winds continuously around the body 5 of the keel 4.

This embodiment has, among others, the particular benefit of encouraging bone growth producing a continuous volume of bone material representing a high fixing power and firmness. This volume of material may equally be produced by a bone substitute, which may be introduced into the drilled hole P.

Figure 3:
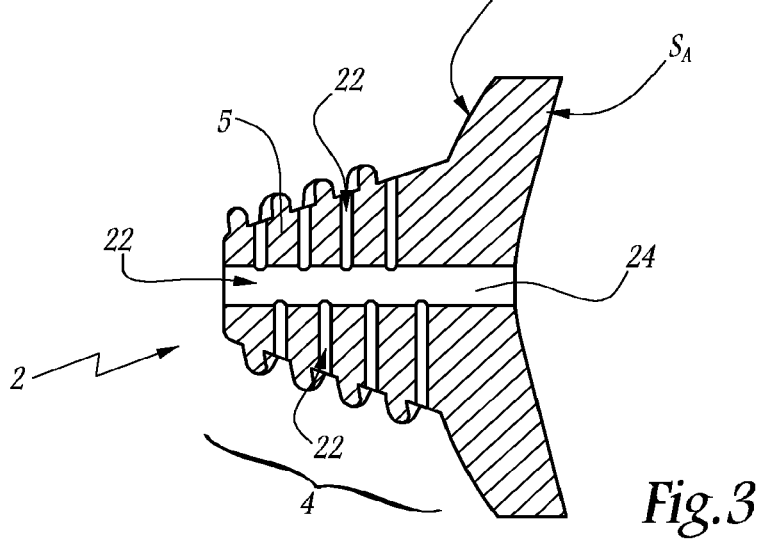
FIG. 3 is a front view of a glenoid component according to a second embodiment of the invention.

In a second embodiment represented in FIG. 3 the body 5 of the keel 4 comprises a network of internal passages 22. These internal passages 22 open onto the external surface of the body 5, preferably between two successive fins 6. They advantageously pass completely through the body of the keel, communicate with each other and are connected to an orifice 24 for injecting a fluid. This injection orifice 24 is preferably situated on the articulation surface $S_A$ of the component 2 and must be used to inject into the internal passages 22 a bone substitute, preferably bioresorbable, or a solution containing growth factors. The injection of a solution containing growth factors has the object of accelerating and encouraging bone growth in the gap induced by the presence of the fins in order to make firm the fixing of the component 2 into the glenoid cavity G.

Figure 4:
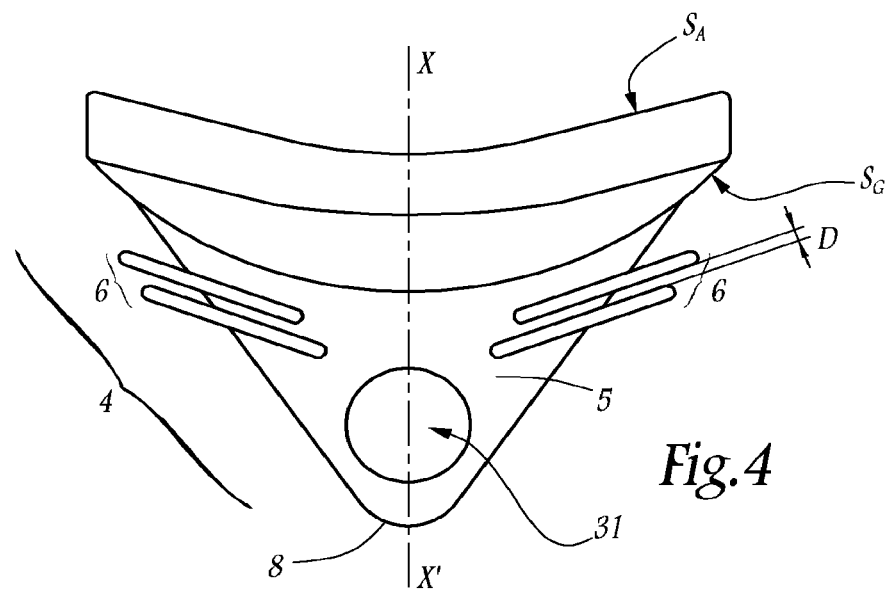
FIG. 4 is a front view of a glenoid component according to a third embodiment of the invention.

In a third embodiment of the invention represented in FIG. 4 the keel 4 includes a series of fins 6, the surfaces 11 and 12 of each fin being parallel to the surfaces of the other fins. The keel 4 can thus have a plurality of parallel fins 6 over a part of its perimeter, as in FIG. 4. As represented in this figure, the fins 6 may be inclined in the direction of the end 8. This inclination makes it possible to facilitate the insertion of the component into the glenoid cavity and to prevent its withdrawal, the fins 6 tending to spread apart in the spongy tissue.

The implantation of such a series of fins 6 makes it possible, among other things, to improve the immobilization of the component 2 in the glenoid cavity G. The distance D between two successive fins of the series, which is defined by the distance between the surface 11 of one of the fins and the surface 12 of the next fin in the series, is chosen in order to optimize the stability of fixing and the efficacy of bone growth. A small distance D between the fins 6 may induce a high stability of fixing and fast bone growth in the gaps, but the bony reinforcement created in this gap will be less firm than a bony reinforcement generated between fins with a greater spacing. The distance D between the two successive fins may be different from one pair of fins to another.

As shown in FIG. 4, the keel 4 may include at least one hole 31 passing completely through the body 5, preferably in a direction corresponding to the smallest dimension of the cross section of the body 5. Like the fins 6, this hole serves to improve the retention of the component by encouraging bone regrowth in the space created.

It will be noted that the presence of such a hole 31 may be considered independently of the presence of the fins 6.

Figure 5A:
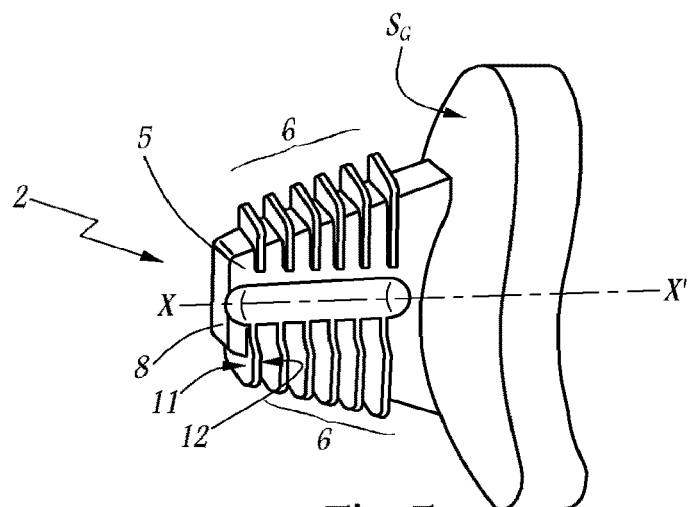
FIG. 5a is a front view of a glenoid component according to a fourth embodiment of the invention.
Figure 5B:
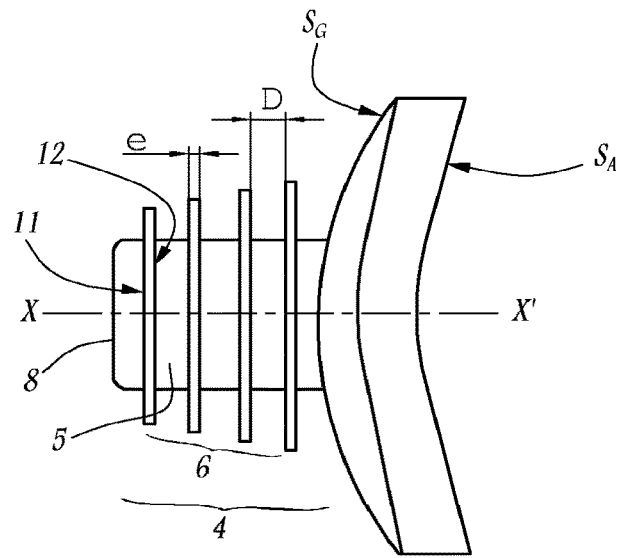
FIG. 5b is a front view of a glenoid component according to a variant of the fourth embodiment of the invention.
Figure 5C:
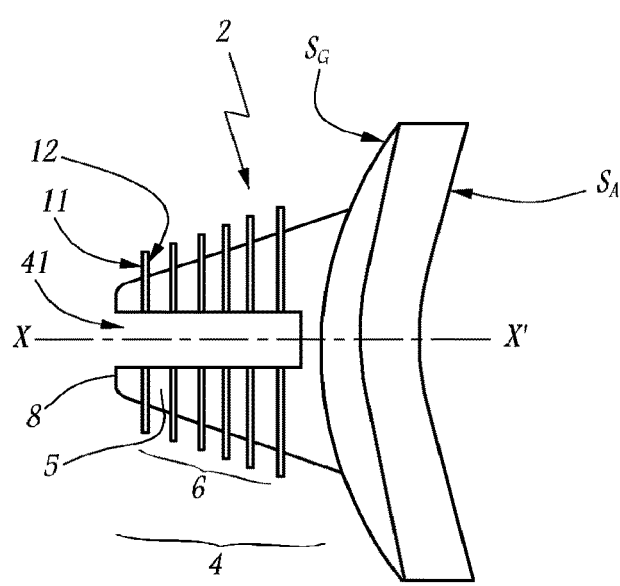
FIG. 5c is a front view of a glenoid component according to a second variant of the fourth embodiment of the invention.

In a fourth embodiment represented in FIGS. 5a, 5b and 5c the fins 6 of the keel 4 are disposed perpendicularly to the longitudinal main axis X-X' of the body 5 of the keel. The surfaces 11 and 12 of the walls constituting the fins are thus contained in planes perpendicular to the longitudinal axis X-X'. This disposition of the fins 6 provides a more efficacious fixing if the forces that are exerted on the component 2 are directed along the longitudinal axis X-X'.

In this regard, the body 5 of the keel 4 may be of parallelepiped shape with the overall external envelope of the keel resembling a truncated cone with an elliptical base or a truncated pyramid, as shown in FIG. 5b. To this end, the width of the fins, i.e. the dimension of their projection from the external surface of the body 5, decreases between the bearing face $S_G$ and the end 8. This increases the stability of the component 2 near the bearing face $S_G$.

The body 5 of the keel 4 may equally have the external shape of a truncated cone with an elliptical base or a truncated pyramid, as shown in FIGS. 5a and 5c, the fins 6 being of identical width. The overall exterior envelope of the keel 4 is then conical. In a variant that is not shown, the body 5 may be frustoconical or pyramidal and the keel 4 have a cylindrical envelope with an elliptical base and vice-versa. The body 5 and/or the external envelope of the keel 4 may equally have an inverted cone or inverted pyramid shape the area of the section of which increases toward the end 8.

As shown in FIG. 5c the body 5 of the keel 4 may include an opening 41 extending along the axis X-X' over a middle part of the body 5. This opening 41 may extend along the axis X-X' over all or part of the body 5. Such an opening enables movement toward each other of the two lateral parts created in this way when inserting the component. The tendency of these two parts to move apart makes it possible to improve the retention of the component.

Figure 6:
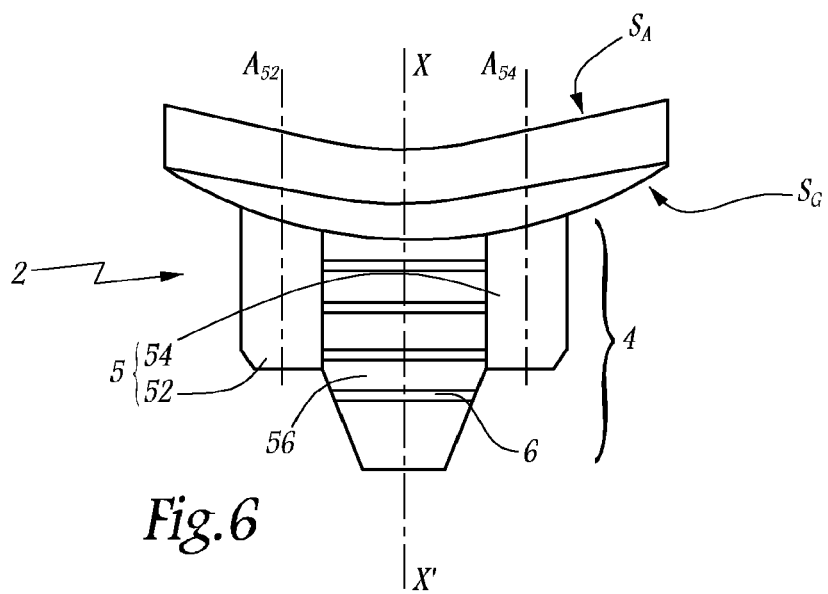
FIG. 6 is a front view of a glenoid component according to a fifth embodiment of the invention.
Figure 7:
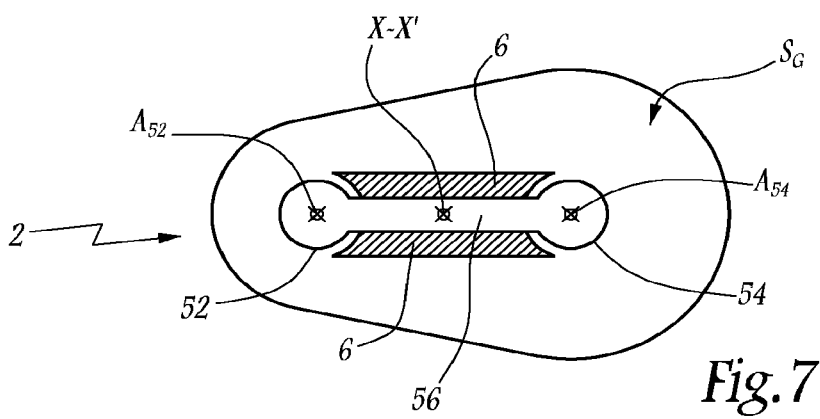
FIG. 7 is a bottom view of the glenoid component from FIG. 6.

In a fifth embodiment of the invention shown in FIGS. 6 and 7, the body 5 of the keel 4 comprises two separate and parallel cylindrical parts 52 and 54. These cylindrical parts, the number of which is not limited, may be of circular section. These cylindrical parts extend from the bearing face $S_G$ along longitudinal parallel axes $A_{52}$ and $A_{54}$. The two cylindrical parts 52 and 54 advantageously extend parallel to the longitudinal main axis X-X' of the body of the keel. Alternatively, the cylindrical parts 52 and 54 may extend along longitudinal axes $A_{52}$ and $A_{54}$ inclined one relative to the other and also relative to the axis X-X'.

Between these two cylindrical parts 52 and 54 extends a central connecting wall 56 on which the fins 6 are implanted. The fins thus extend between the two cylindrical parts 52 and 54.

The dimensions of the section of these cylindrical parts 52 and 54 correspond to the dimensions of drilled holes P produced in the glenoid cavity G for implanting the component 2. If these cylindrical parts 52 and 54 are of circular section, the dimensions taken into account to define the geometry of the cylindrical parts is that of the drill used to produce the drilled holes P in the glenoid cavity G. A slightly tight fit may be chosen in order to obtain greater stability of the implantation of the component 2.

In this embodiment, the fins 6 may be made of a deformable material able to exert a pressure on the walls of a slot produced in the glenoid cavity G to connect the two drilled holes P. For example, the fins 6 may be made of a polymer material or polyethylene.

Figure 8:
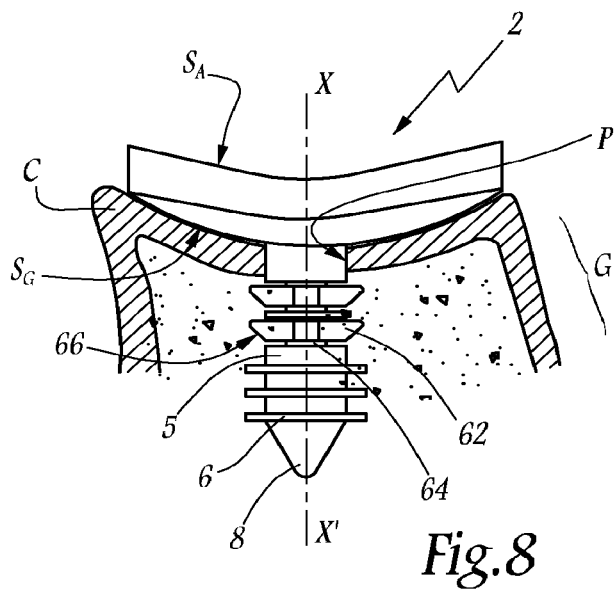
FIG. 8 is a front view of a glenoid component according to a sixth embodiment of the invention implanted in the glenoid cavity of a shoulder.

In a sixth embodiment of the invention shown in FIG. 8 the body 5 of the keel 4 includes at least one elastic ring 62. The function of this elastic ring 62 is to exert pressure on the wall of the drilled hole produced in the glenoid cavity G in order to strengthen the firmness of the implantation.

The elastic ring 62 is housed in a peripheral external groove 64 formed on the body 5 of the keel 4 that extends over the whole of the perimeter of the keel.

The exterior dimensions of the elastic ring 62 in the relaxed configuration are greater than the dimensions of the drilled hole P produced in the glenoid cavity G. Moreover, the elastic ring 62 has an oblique peripheral edge 66 converging toward the longitudinal main axis X-X' of the body 5 of the keel 4 in the direction of the end 8 of the keel. When inserting the glenoid component 2 in the glenoid cavity G, this particular geometry enables sliding of the cortical wall C of the glenoid cavity along the oblique edge 66 of the elastic ring 62 and retraction of the elastic ring into the peripheral groove 64. Once the component has been inserted in the glenoid cavity G, the elastic ring 62 relaxes into the spongy part of the glenoid cavity G, blocking the movements of the component 2 along the longitudinal axis X-X' of the body 5 of the keel 4 thanks to its exterior dimensions being greater than the dimensions of the drilled hole in the cortical wall. A plurality of elastic rings 62 may be used in this embodiment.

It will be noted that the presence of such a ring 62 may be considered independently of the presence of the fins 6.

Figure 9:
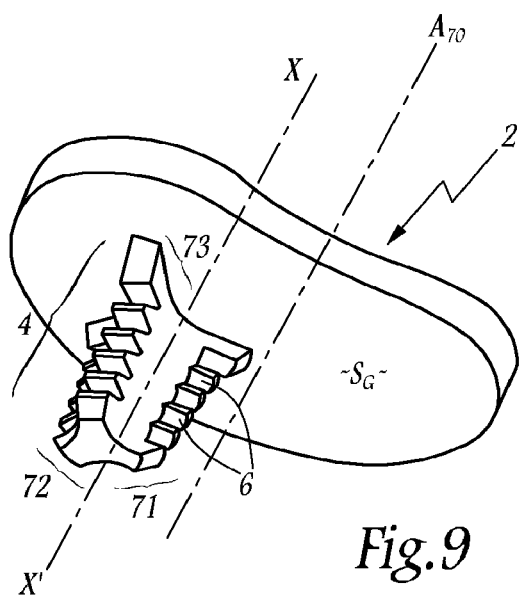
FIG. 9 is a perspective view of a glenoid component according to a seventh embodiment of the invention.

In a seventh embodiment of the invention shown in FIG. 9, the body 5 of the keel 4 has on a plane perpendicular to its longitudinal axis X-X' a star-shaped cross section including at least three branches. The keel 5 then consists of at least three contiguous flanges 71, 72 and 73 each oriented relative to the other two at two substantially equal angles. The fins 6 are implanted on the three contiguous flanges 71, 72 and 73.

This keel geometry makes it possible to obtain increased stability about the longitudinal axis X-X' by preventing rotation of the glenoid component 2 about that axis.

The position of the keel 4 on the bearing face $S_G$ may then be eccentric relative to an axis $A_{70}$ passing through the geometrical centre of the face $S_G$ and substantially perpendicular to that surface.

Figure 10:
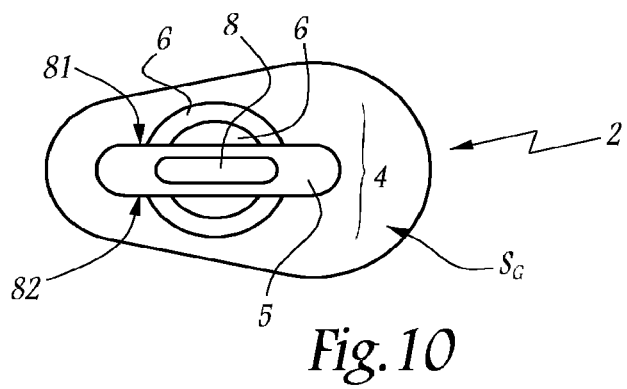
FIG. 10 is a perspective view of a glenoid component according to an eighth embodiment of the invention.

In an eighth embodiment of the invention shown in FIG. 10 the fins 6 have surfaces 11 and 12 with semicircular free edges. If the body 5 has substantially the shape of a substantially plane thick wall, the fins 6 may extend from each side 81 and 82 of that wall.

Figure 11:
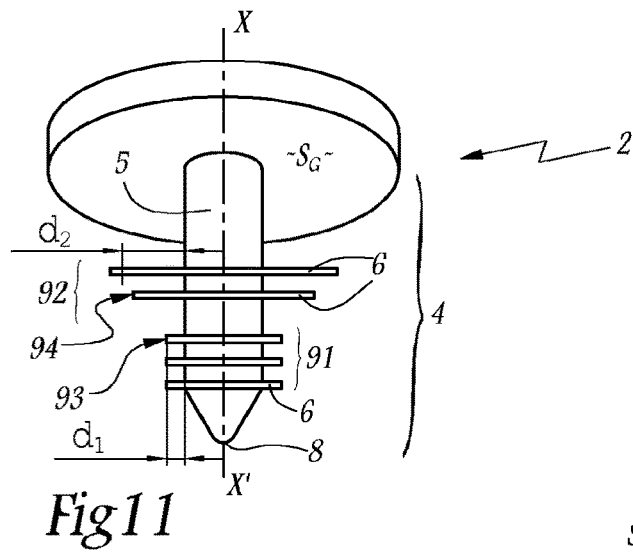
FIG. 11 is a perspective view of a glenoid component according to a ninth embodiment of the invention.

In a ninth embodiment shown in FIG. 11, the keel 4 comprises two separate series 91 and 92 of fins 6. These two series of fins are staggered along the longitudinal main axis X-X' of the body 5. The series 91 of fins adjoins the end 8 of the keel and the second series 92 of fins is on the longitudinal axis X-X' between the first series 91 of fins and the bearing face $S_G$ on the glenoid cavity.

The series 92 of fins is wider than the series 91 of fins, i.e. the average distance $d_1$ between the external surface of the body 5 of the keel 4 and the free edge 93 of the fins of the series 91 is less than the distance $d_2$ between the external surface of the body 5 of the keel 4 and the free edge 94 of the fins of the series 92.

This particular geometry makes it possible for the fins of the series 92 to fulfil the primary fixing function, which consists in stable implantation of the component in the glenoid cavity, thanks to their width being greater than those of the fins of the series 91. Thanks to their narrow width, the first fins 91 fulfil the secondary fixing function by virtue of bone growth in the gaps that they delimit.

Figure 12:
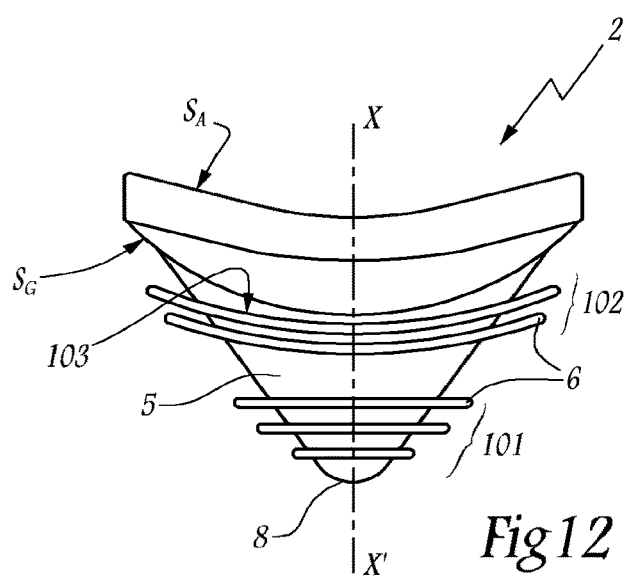
FIG. 12 is a perspective view of a glenoid component according to a tenth embodiment of the invention.
Figure 13:
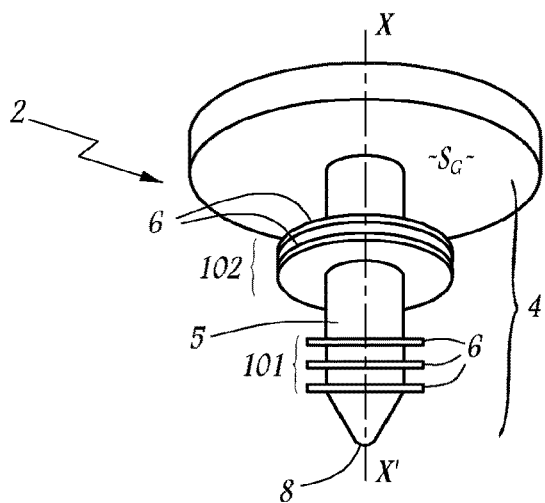
FIG. 13 is a side view of the glenoid component from FIG. 12.

In a tenth embodiment of the invention shown in FIGS. 12 and 13 the keel 4 of the glenoid component 2 comprises two series 101 and 102 of fins 6, the series 102 of fins closer to the bearing face $S_G$ having surfaces geometrically similar to the bearing surface $S_G$. The series 102 of fins thus has surfaces 103 that may be superposed on the bearing face $S_G$ of the glenoid cavity G. This geometry enables these fins to exert forces on the glenoid cavity G in the same direction as the bearing forces exerted by the face $S_G$, which creates increased stability of the fixing of the glenoid component 2.

Figure 14:
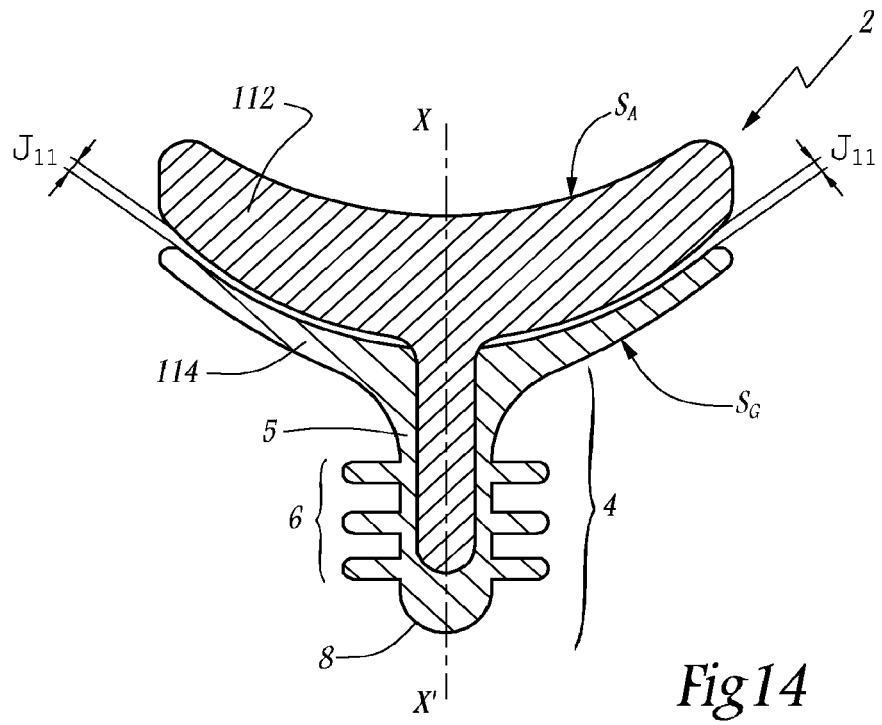
FIG. 14 is a section on a median plane of a glenoid component according to an eleventh embodiment of the invention.

In an eleventh embodiment of the invention shown in FIG. 14 the glenoid component 2 is made up of two elements. One element 112, preferably made of a polymer material and carrying the articulation surface $S_A$, is mounted in a preferably metal shell 114. The metal shell 114 carries the bearing face $S_G$ of the socket and forms a part of the body 5 of the keel 4. The metal shell 114 is intended to be implanted in glenoid cavity G of the shoulder and to this end includes fins 6. The shell 114 may equally be made of ceramic and have a partly porous surface.

In order to provide a space for movement of the polymer material element 112, the geometry of the metal shell 114 provides a clearance $J_{11}$ between the surfaces of contact between the polymer element 112 and the metal shell 114 at the level of an area of the glenoid component 2 situated outside the glenoid cavity G. By authorizing this freedom of movement of the polymer element 112, plastic deformation of that element is prevented and the forces exerted on the component 2 where it is implanted in the glenoid cavity G are reduced, which makes it possible to increase its service life and stability.

Figure 15:
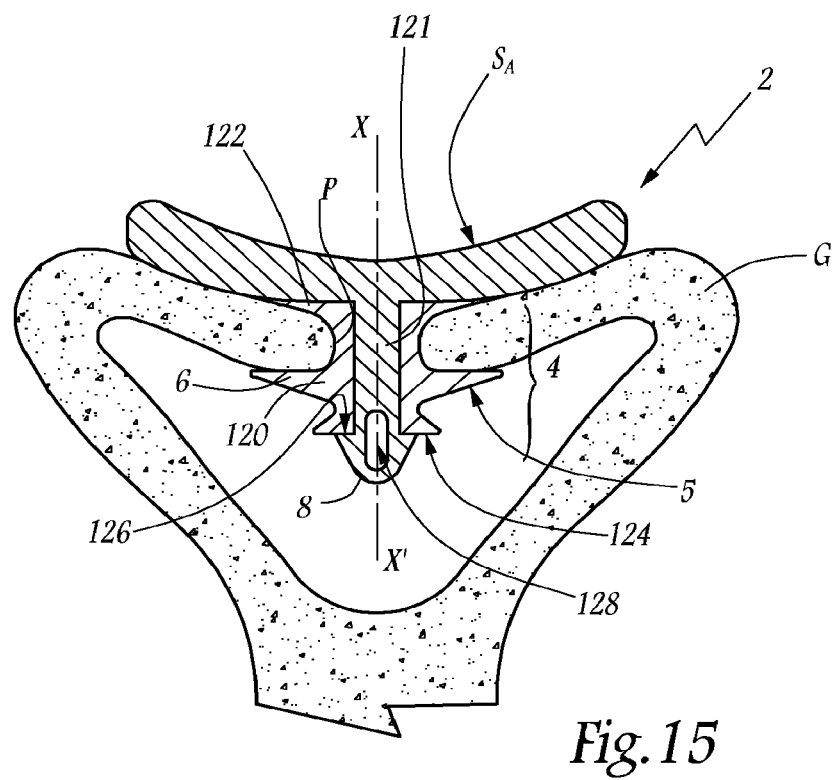
FIG. 15 is a section in a median plane of a glenoid component according to a twelfth embodiment of the invention implanted in the glenoid cavity of a shoulder socket.

In a twelfth embodiment of the invention shown in FIG. 15 the body 5 of the keel 4 comprises a flexible sheath 120 surrounding a rod 121 in one piece with the face $S_G$ on which the fins 6 are implanted. This elastic sheath 120, which may be made of a polymer material, comprises an end rim 122 adapted to bear on the glenoid cavity G. The part of the flexible sheath 120 intended to be implanted in the glenoid cavity G is elastic so as to be retracted in the relaxed configuration. In this way, the flexible sheath 120 is inserted into the hole P drilled in the glenoid cavity G. The rod 121 is then inserted in the flexible sheath 120, enlarging it in order for its fin or fins 6 to spread apart in the glenoid cavity G to lock the implantation of the glenoid component 2.

To counter the tendency of the flexible sheath 120 to expel the rod 121, having the rod protrude from the flexible sheath 120 and providing on it a shoulder 126 widening the part of the rod projecting from the flexible sheath may be envisaged. In order to block movements in translation of the rod 121 in the flexible sheath 120, this shoulder 126 bears against the end 124 of the flexible sheath anchored in the glenoid cavity G.

The end 8 of the body 5 of the keel 4 carried by the rod 121 advantageously includes at least one hole 128 the function of which is to encourage bone growth in the space created in order to increase the stability of the fixing.

In a variant that is not shown, the glenoid component 2 may include, in addition to the anchor keel 4, an eccentric peg projecting from the face $S_G$ and making it possible to improve the fixing of the component in the socket G, in particular blocking its rotation.

Of course, the features of the embodiments shown may be combined with each other in the context of the present invention.

The invention claimed is:

1. A shoulder prosthesis glenoid component comprising:
    an articulation surface that is concave to cooperate with a humeral head;
    an opposite surface that is opposite to the articulation surface and is configured to mate with a glenoid cavity of a shoulder;
    a keel protruding from the opposite surface, the keel including a body that extends from the opposite surface at a position that is eccentric relative to an axis passing through a geometrical center of the opposite surface; and
    at least one internal passage extending between an external surface of the body and an orifice situated on the articulation surface, wherein
    the opposite surface extends continuously from the keel to a periphery of the opposite surface, and
    the keel further includes at least one fin that is deformable and projecting radially from a portion of a perimeter of the body.

2. The shoulder prosthesis glenoid component according to claim 1, wherein the body of the keel has, in a cross section perpendicular to the axis, a non-circular peripheral contour configured to block rotation of the glenoid component.

3. The shoulder prosthesis glenoid component according to claim 1, wherein the at least one fin has a helicoidal shape and winds around the body.

4. The shoulder prosthesis glenoid component according to claim 1, wherein the at least one fin includes a first surface and a second surface, the first surface between the opposite surface and the second surface, the first and second surfaces extending in a plane substantially perpendicular to a longitudinal axis of the body.

5. The shoulder prosthesis glenoid component according to claim 1, wherein the body includes at least two separate cylindrical portions, respective axes of which are parallel to each other and between which the at least one fin extends.

6. The shoulder prosthesis glenoid component according to claim 1, wherein the body includes at least one external peripheral groove and an elastic ring in the at least one external peripheral groove.

7. The shoulder prosthesis glenoid component according to claim 1, wherein the body has a star-shaped cross section including at least three branches.

8. The shoulder prosthesis glenoid component according to claim 1, wherein the at least one fin has a semicircular peripheral contour.

9. The shoulder prosthesis glenoid component according to claim 1, wherein the at least one fin is a first series of parallel fins.

10. The shoulder prosthesis glenoid component according to claim 9, wherein the keel further includes a second series of parallel fins, of width greater than that of the first series of parallel fins and located closer to the opposite surface along a longitudinal main axis of the body than the first series of parallel fins.

11. The shoulder prosthesis glenoid component according to claim 10, wherein the first series of parallel fins or the second series of parallel fins have a shape that is a same shape of the opposite surface.

12. The shoulder prosthesis glenoid component according to claim 1, wherein the articulation surface is carried by an element adapted to be mounted in a metal shell of the component carrying the opposite face and in one piece with the body of the keel.

13. The shoulder prosthesis glenoid component according to claim 1, wherein the body of the keel includes a flexible sheath provided with the at least one fin into which a portion in one piece with the opposite surface is adapted to fit.

14. The shoulder prosthesis glenoid component according to claim 1, wherein the at least one fin is made of polyethylene.

15. The glenoid component according to claim 1, wherein the keel includes a cavity between the at least one fin and the opposite surface, the cavity configured to encourage locking of the shoulder prosthesis in the glenoid cavity by bone growth in the cavity.

16. The shoulder prosthesis glenoid component according to claim 1, further comprising an eccentrically located peg projecting from the opposite surface.

17. The shoulder prosthesis glenoid component according to claim 1, wherein the body of the keel includes a flange configured to prevent rotation of the glenoid component about the axis.

18. The shoulder prosthesis glenoid component according to claim 17, wherein the body of the keel includes at least three contiguous flanges.

19. The shoulder prosthesis glenoid component according to claim 17, wherein the at least one fin projects from the flange.

20. The shoulder prosthesis glenoid component according to claim 18, wherein the at least three contiguous flanges are contiguous at a central portion of the body and spaced apart at the perimeter of the body.

21. The shoulder prosthesis glenoid component according to claim 20, wherein the at least one fin includes a plurality of fins spaced apart along a medial-lateral direction of the body.

22. The shoulder prosthesis glenoid component according to claim 20, wherein the keel includes a concave surface extending between an outer portion of a first flange of the at least three contiguous flanges and an outer portion of a second flange of the at least three contiguous flanges.

23. The shoulder prosthesis glenoid componet according to claim 1, wherein the at least one internal passage open onto the external surface of the body between two successive fins.

24. The shoulder prosthesis glenoid component according to claim 1, wherein the at least one internal passage comprise a network of internal passages.

\* \* \* \* \*